(12) United States Patent
Meriheinä

(10) Patent No.: US 10,729,349 B2
(45) Date of Patent: Aug. 4, 2020

(54) METHOD AND APPARATUS FOR MONITORING HEARTBEATS

(71) Applicant: MURATA MANUFACTURING CO., LTD., Nagaokakyo-shi, Kyoto (JP)

(72) Inventor: Ulf Meriheinä, Söderkulla (FI)

(73) Assignee: MURATA MANUFACTURING CO., LTD., Nagaokakyo-shi, Kyoto (JP)

( * ) Notice: Subject to any disclaimer, the term of this patent is extended or adjusted under 35 U.S.C. 154(b) by 208 days.

(21) Appl. No.: 15/722,308

(22) Filed: Oct. 2, 2017

(65) Prior Publication Data
US 2018/0092564 A1 Apr. 5, 2018

(30) Foreign Application Priority Data
Oct. 5, 2016 (FI) ..................................... 20165748

(51) Int. Cl.
*A61B 5/04* (2006.01)
*A61B 5/0444* (2006.01)
(Continued)

(52) U.S. Cl.
CPC .......... *A61B 5/0444* (2013.01); *A61B 5/0006* (2013.01); *A61B 5/024* (2013.01);
(Continued)

(58) Field of Classification Search
CPC . A61B 5/0444; A61B 5/0006; A61B 5/02141; A61B 5/024; A61B 5/02411;
(Continued)

(56) References Cited

U.S. PATENT DOCUMENTS 5,596,993 A * 1/1997 Oriol .................. A61B 5/02411
128/925
2001/0014776 A1 8/2001 Oriol et al.
(Continued)

FOREIGN PATENT DOCUMENTS

EP 2 737 848 A2 6/2014
JP 2001017403 A 1/2001
(Continued)

OTHER PUBLICATIONS

Finnish Search Report dated Apr. 27, 2017 corresponding to Finnish Patent Application No. 20165748.
(Continued)

*Primary Examiner* — Catherine M Voorhees
*Assistant Examiner* — Roland Dinga
(74) *Attorney, Agent, or Firm* — Squire Patton Boggs (US) LLP (57) ABSTRACT

A ballistocardiographic method and monitoring system calculates an indicator of the average heart rate of a test subject within a time interval. The test subject may be a fetus inside a mother's belly, or infant lying in the same bed as an adult. The monitoring system comprises a recoil surface and an acceleration sensor in contact with the recoil surface. A control unit identifies in the time domain the characteristics of the adult's heartbeat during the time interval. The output signal is then transformed to the frequency domain across the time interval and the signal is screened with the adult heartbeat characteristics. The indicator is then calculated from the screened signal in the frequency domain. The control unit monitors the indicator of the infant or fetus heart rate and may provide an alert if the indicator value drops very rapidly, or falls below a predetermined threshold value.

8 Claims, 4 Drawing Sheets

(51) Int. Cl.
  *A61B 5/024* (2006.01)
  *A61B 5/11* (2006.01)
  *A61B 5/00* (2006.01)
  *A61B 5/021* (2006.01)

(52) U.S. Cl.
  CPC ...... *A61B 5/02141* (2013.01); *A61B 5/02411* (2013.01); *A61B 5/1102* (2013.01); *A61B 5/72* (2013.01); *A61B 5/02405* (2013.01); *A61B 5/4362* (2013.01)

(58) Field of Classification Search
  CPC ..... A61B 5/1102; A61B 5/72; A61B 5/02405; A61B 5/4362
  See application file for complete search history.

(56) References Cited

U.S. PATENT DOCUMENTS

| | | |
|---|---|---|
| 2001/1114776 | 8/2001 | Oriol et al. |
| 2006/0155175 A1* | 7/2006 | Ogino ............... A61B 5/02438 600/301 |
| 2006/0229518 A1 | 10/2006 | Ofek |
| 2006/0241510 A1 | 10/2006 | Halperin et al. |
| 2008/0077020 A1 | 3/2008 | Young et al. |
| 2010/0305481 A1 | 12/2010 | Igney et al. |
| 2011/0112442 A1 | 5/2011 | Meger et al. |
| 2012/0150010 A1 | 6/2012 | Hayes-Gill et al. |
| 2013/0006132 A1 | 1/2013 | Brody et al. |

FOREIGN PATENT DOCUMENTS

| | | |
|---|---|---|
| JP | 2009501557 A | 1/2009 |
| JP | 2009532072 A | 9/2009 |
| WO | WO 96/15713 A1 | 5/1996 |
| WO | 2007/052108 A2 | 5/2007 |
| WO | 2010/004502 A1 | 1/2010 |
| WO | 2010/067294 A1 | 6/2010 |
| WO | 2010/145009 A1 | 12/2010 |
| WO | WO 2015/036925 A1 | 3/2015 |
| WO | 2015/103451 A9 | 7/2015 |

OTHER PUBLICATIONS

R. Mantel et al., "Computer Analysis of Antepartum Fetal Heart Rate: 2. Detection of Accelerations and Decelerations," International Journal of Bio-medical Computing, Elsevier Science Publishers, vol. 25/4, May 1, 1990, pp. 273-286.

Mojtaba Jafari Tadi et al., "A Real-Time Approach for Heart Rate Monitoring Using a Hilbert Transform in Seismocardiograms", Institute of Physics and Engineering in Medicine, Physiol. 2016, pp. 1885-1909.

Matthias Daniel Zink et al., "Heartbeat Cycle Length Detection by a Ballistocardiographic Sensor in Atrial Fibrillation and Sinus Rhythm", Hindawi Publishing Corporation, BioMed Research International vol. 2015, Article ID—840356, 10 pages.

European Search Report application No. EP 17 19 2008 dated Dec. 20, 2017.

* cited by examiner

METHOD AND APPARATUS FOR MONITORING HEARTBEATS

FIELD OF THE DISCLOSURE

The present disclosure relates to monitoring of heartbeats, particularly to monitoring of fetus and infant heartbeats with ballistocardiographic measurements. The present disclosure further relates to an analysis method and an apparatus which allow the weak ballistocardiographic signals caused by infant and fetus heartbeats to be distinguished from more dominant signal components, such as an adult's heartbeat.

BACKGROUND OF THE DISCLOSURE

Ballistocardiographic measurements conducted with accelerometers or angular rate sensors measure the movements of a human body which arise from the pumping action of the heart. Two mechanical effects associated with heartbeats can typically be detected: a recoil effect on the chest caused by the pumping motion itself, and a recoil effect on the whole body caused by the ejection of blood into arteries across the body. Both of these recoil effects will be called "heartbeat recoils" in this disclosure.

Most movements which human beings generate on their own volition are stronger and more extensive than a heartbeat recoil. Ballistocardiographic measurements therefore typically require that the person on whom the measurement is conducted should be at rest, preferably lying down. Good measurement data can often be obtained when the person is sleeping.

Recoil effects can be detected either directly from the body or indirectly from a surface which is in physical contact with the body and moves with it. This surface may, for example, be a mattress where the person is resting. When the test subject is a fetus, the surface may be the mother's belly. In this disclosure, the term "recoil surface" will be used as a general term for a surface where a ballistocardiographic measurement can be performed.

Even when the person on whom a ballistocardiographic measurement is conducted is lying still, heartbeat recoils are very small movements and the sensors used in these measurements must be very sensitive. This problem has been resolved with modern MEMS acceleration sensors and gyroscopes, which have sufficiently high resolution for ballistocardiographic measurements.

The interpretation of ballistocardiographic measurements is aided by the periodicity of the heartbeat. The person on whom the measurement is performed may move around as she rests or sleeps, but such movements are not periodic. The periodic heartbeat recoil signal, which usually exhibits a frequency of 50-200/minute, can be distinguished from non-periodic movements and from periodic movements with frequencies outside of this range, such as respiratory movement. However, if two separate heartbeat recoil components are present in the same ballistocardiographic signal, they can be hard to distinguish from each other.

The heartbeats of newborn infants and unborn fetuses are often monitored for medical reasons. A drop in their heart rate indicates a decrease in oxygen saturation in the blood stream. If an infant's heart rate drops below 60 beats per minute, he or she may be at critical risk of cot death. A drop in a fetus' heart rate is an indication of similar risks. Immediate action is then required to avoid a fatal outcome.

Continuous automated monitoring of infant and fetus heartbeats, especially during sleep, is a reliable preventive measure against such risks. Automated monitoring systems can comprise an alarm function which alerts a nearby adult of a sudden drop in an infant's or a fetus' heart rate.

Fetus heart rates can be monitored in hospitals with ultrasonography and infant heart rates with sensors placed on the infant's body. However, neither of these methods can be easily implemented for continuous heart rate monitoring at home. Ultrasonography requires complex equipment and a human operator, while wearable sensors can be uncomfortable to an infant.

In contrast, automated ballistocardiographic monitoring of infant and fetus heartbeats can be performed continuously without inconvenience to the infant or fetus. A ballistocardiographic sensor can, for example, be attached to the bed or mattress where an infant sleeps, or to the belly of a pregnant mother.

Ballistocardiographic measurements can be performed on a lone infant sleeping in a bed with methods known from the prior art. Document US20080077020 A1 discloses a method and apparatus for monitoring the vital signs of an infant sleeping in a crib. The method utilizes a ballistograph, which in this case is a fluid-filled pad or mechanical plate equipped with pressure sensors or other sensors which record the heart rate.

However, infants often sleep in the same bed as one or more adults. This produces a measurement problem: the weak heartbeat recoils caused by an infant's heart cannot be read directly from the ballistocardiographic signal because they are mixed with adult heartbeat recoils. The same measurement problem is present when fetus heartbeats are measured with a ballistocardiographic sensor. The mother's heartbeat recoil is significantly stronger than the fetus' heartbeat recoil.

In the presence of two heartbeat recoils, there will be two overlapping periodic components in the ballistocardiographic signal. It is not possible to distinguish the much weaker signal caused by an infant's heartbeat recoil from the stronger signal caused by an adult with prior art methods, such as the one disclosed in document US20080077020 for monitoring a lone infant.

Document US20100305481 A1 discloses a system for automatically monitoring the movement of a fetus. The method is based on detecting the movements and the heart-rate of the mother through ballistocardiographic measurements, and using this information to distinguish the fetus' movements from the mother's movements. However, this document does not disclose a measurement of the fetus' heart rate.

Document WO2015036925 A1 discloses methods for determining the heart rate and respiration rate of a person from ballistocardiographic data measured from an acceleration sensor. But in situations where two heartbeats are present, one stronger than the other, only the stronger heartbeat can be identified with this method from the measurement signal.

BRIEF DESCRIPTION OF THE DISCLOSURE

An objective of the present disclosure is to provide a method and an apparatus for implementing the method so as to overcome or at least alleviate some of the problems mentioned above.

The objectives of the disclosure are achieved by a method and an arrangement which is characterized by what is stated in the independent claims. The preferred embodiments of the disclosure are disclosed in the dependent claims.

The disclosure is based on the idea of measuring a ballistocardiographic signal with an acceleration sensor attached either to the belly of a pregnant mother or to a surface on which an infant and an adult are lying. Gyroscopes, which measure angular rate, may also be used. The sensor output signal is continuously monitored. By analysing the signal in the time domain, where the signal has been stored as a function of time, the basic characteristics of the dominant periodic signal component, such as the adult's heart rate and respiration rate, can be determined.

The signal is then transformed to the frequency domain, for example with a Fourier transformation. In simplified terms, a transformation into the frequency domain counts the signal peaks which occur at regular time intervals. Non-periodic components, regardless of their strength, produce few counts or no counts at all. The height of the transformed signal in the frequency domain at a given frequency f is then determined by counted peaks in the time domain at the given frequency f and by their amplitudes. Weak but periodic signal components, which may be difficult to detect in the time domain, become prominent in the frequency domain where non-periodic data is extinguished.

The signal component arising from a fetus or infant heartbeat recoil can therefore in the frequency domain be distinguished from non-periodic noise which partly conceals the presence of this component in the time domain. However, the infant or fetus heartbeat recoil must also be distinguished from the adult heartbeat recoil in the frequency domain, as well as from the higher harmonics of the adult heart rate and respiration rate, which become visible in the frequency domain. To distinguish the infant or fetus heart rate, the adult heart rate and respiration rate can first be determined in the time domain before the transformation. These characteristic frequencies can then be screened in the frequency domain when an indicator of the fetus' or infant's heart rate is calculated.

An advantage of the method and arrangement of this disclosure is that infant or fetus heart rates can be monitored continuously, even in the presence of an adult, with a non-invasive, versatile and simple measurement which comprises only one sensor.

The method and apparatus described in this disclosure differ from ultrasonographic or sensor-based heart rate measurements in that they produce an indicator of the test subject's average heart rate within a time interval. In other words, they produce an estimate derived from a calculation, not a direct measurement of the momentary heart rate. Direct measurements of momentary heart rate facilitate real-time monitoring, but such measurements cannot be performed continuously without inconvenience. Non-invasive measurement is an important objective for the method and apparatus of the present disclosure. They produce heart rate indicators which have sufficient accuracy for continuous monitoring purposes.

The term "indicator" refers in this disclosure to a numerical value estimated with the method and apparatus described in this disclosure. This value is calculated from series of measurement data obtained during the time interval from an acceleration sensor or gyroscope, as described in more detail below. The indicator is an average value because data points from the entire time interval may be included in its calculation. The indicator may be a recursive weighted average, so that one element of each new indicator value (except the first) is an earlier indicator value.

Although this disclosure primarily describes measurements performed on human test subjects, the method and apparatus described in this disclosure may also be used in situations where one or both of the test subjects is an animal. For example, the measurement may be performed on a human child and a pet animal sleeping in the same bed, or on an infant animal and adult animal sleeping on the same surface.

BRIEF DESCRIPTION OF THE DRAWINGS

This disclosure will be described in greater detail by means of preferred embodiments with reference to the accompanying drawings, in which.

DETAILED DESCRIPTION OF THE DISCLOSURE

Figure 1:
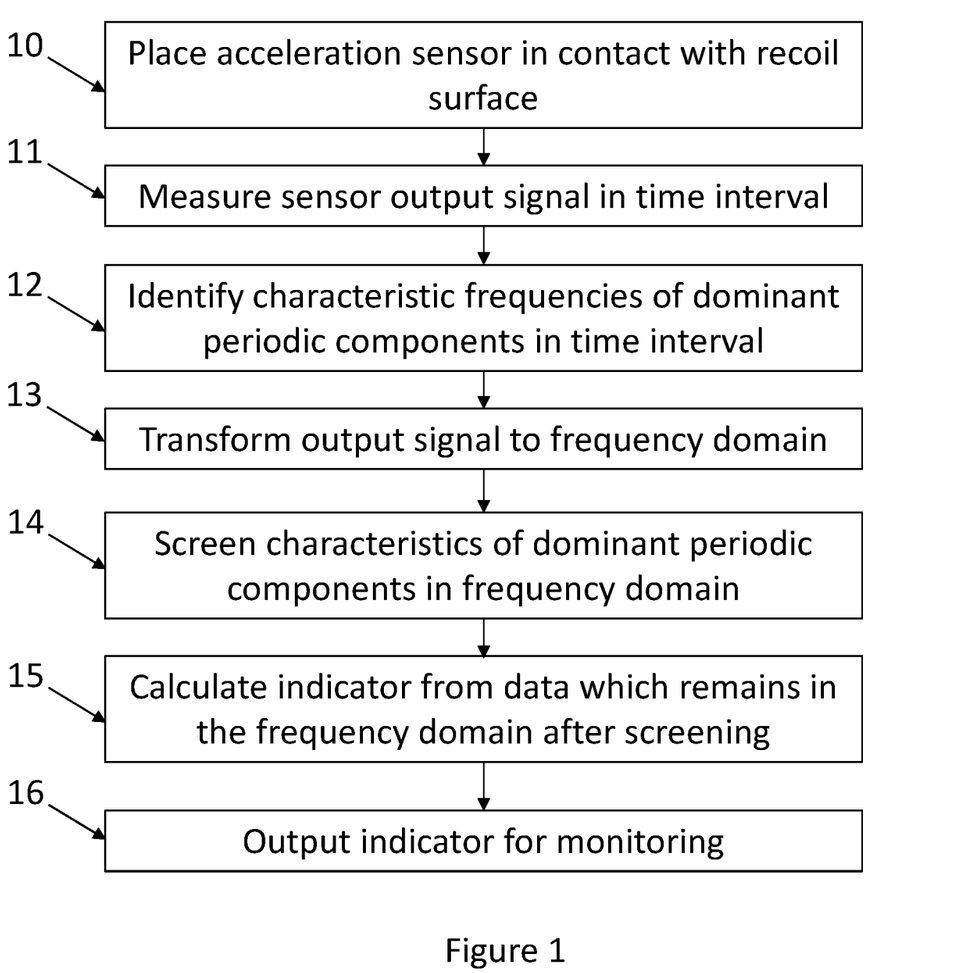
FIG. 1 illustrates a method described in this disclosure.

FIG. 1 shows a schematic illustration of a method for monitoring the heart rate of a test subject. The method comprises placing an acceleration sensor in contact with a recoil surface which is in contact with the test subject (stage 10), and measuring a sensor output signal in multiple time intervals (stage 11). An indicator of the average heart rate of the test subject in a time interval is calculated (stage 15) from the sensor output signal measured in that time interval, and the indicator is output (stage 16) for monitoring. For calculating the indicator, characteristic frequencies of dominant periodic components in the sensor output signal are identified (stage 12) in the time domain during the time interval, the output signal is transformed (stage 13) to the frequency domain across the time interval, the characteristic frequencies of dominant periodic components in the frequency domain are screened (stage 14), and the indicator is calculated (stage 15) from the data which remains in the frequency domain after screening.

In this disclosure the terms "signal" and "measurement data" both refer to acceleration-dependent output values measured from the acceleration sensor. "Measurement data" is used as a general term for any set of measured values, while the term "signal" refers to a time-stamped series of measurement data. In other words, each individual measurement result is marked with the time when it was measured, and together these measurement results constitute a signal when they are ordered chronologically. A signal can be presented in the time domain by showing measurement results as a function of time, and it can be transformed to the frequency domain with a Fourier transformation, for example.

In this disclosure the term "test subject" refers primarily to a child, an infant or an unborn fetus. However, as described under "further examples" below, the method presented in this disclosure can with some modifications also be implemented for an adult test subject resting on the same recoil surface as another adult. In its broadest meaning the term "test subject" therefore encompasses human beings of any age, including unborn fetuses.

A prerequisite for a successful ballistocardiographic measurement is that the recoil surface is moved by heartbeat recoils. The term "recoil surface" can therefore refer to any surface which undergoes movement due to heartbeat recoils.

In the first embodiment the term refers primarily to the outside of a pregnant mother's belly, where the heartbeat recoil of both mother and fetus can be detected. An acceleration sensor or gyroscope may be placed in contact with the recoil surface with an elastic strap, belt, band or temporary glue. The sensor may be a linear acceleration sensor, but gyroscopes can also be used because the heartbeat recoil produces a small twist on the recoil surface which can be recorded as a change in angular rate. The contact between the recoil surface and the test subject is indirect in this embodiment because at least the mother's stomach muscles and uterus are positioned between the outside of the belly and the fetus. However, these intervening objects are sufficiently elastic to transfer fetus heartbeat recoils to the recoil surface.

In the second embodiment the term "recoil surface" can refer to a bed, crib, mattress, stretcher or any other surface on which a test subject can lie. In this embodiment the test subject may lie on the recoil surface. In this case contact between the test person and the recoil surface can mean either that the test person's skin is in direct contact with the recoil surface, or that the test person makes indirect contact with the recoil surface through intervening objects such as clothes, sheets or a mattress. The recoil surface should be elastic or movable to some degree so that ballistocardiographic signals can be recorded. Any intervening objects between the test person and the recoil surface should also be sufficiently elastic or movable to transfer heartbeat recoils from the test subject to the recoil surface. The acceleration sensor may be placed in contact with the recoil surface with a glue, tape or with mechanical fastening means such as bolts or screws.

If an infant and adult are lying on a bed which is rigidly fixed to the floor or to a wall, the acceleration sensor cannot be fixed to the bed frame because the floor or wall will not allow any elastic energy transfer from the infant's body to the bed frame. In this case the mattress may instead be chosen as a recoil surface, because it will transmit the heartbeat recoil elastically to the sensor. On the other hand, if the bed is for example a hospital bed mounted on wheels, the bed may move sufficiently with each heartbeat recoil, and the sensor can then be attached directly to the bed.

Although the first embodiment relates to measuring of fetus heartbeats and the second to infant heartbeats, the two embodiments are not categorically different. In particular, it is possible to measure fetus heartbeat recoils with a sensor which has been placed on the bed or mattress on which the mother is resting, without fastening the sensor directly to the mother's belly. Some mothers may prefer this measurement setup if they dislike the inconvenience caused by the sensor. This disclosure will describe fetus heartbeat recoil measurement only in the first embodiment, but it should be understood that fetus heartbeat recoils may also be measured with the methods described in the second embodiment.

The acceleration sensor can usually be placed so that one or more of its measurement axes are parallel to the recoil surface, but parallel alignment is not a necessary requirement for obtaining a good ballistocardiographic signal.

The heartbeat recoil in a human body is stronger in the lengthwise direction than in the breadthwise direction, because most major arteries in the body are oriented lengthwise. Consequently, heartbeat recoils should preferably be measured in the lengthwise direction.

When ballistocardiographic measurements are conducted on a grown child or an adult lying on a (more or less narrow) horizontal support, a one-axis acceleration sensor which measures acceleration in the lengthwise direction of the support may be sufficient. However, the method and apparatus of the present disclosure are preferably implemented with a two-axis acceleration sensor because fetuses can orient their bodies in different directions. Infants may also turn their bodies in any direction if they sleep in adult-size beds. A two axis sensor is therefore preferred because it can measure heartbeat recoils in any direction in the plane of the recoil surface.

In this disclosure, the term "dominant periodic components" refers primarily to signal components arising from the heartbeat and respiration of an adult human being. However, periodic noise may also enter the signal through mechanical apparatuses which are in physical contact with the recoil surface. All forms of dominant periodic components can be distinguished from test subject heartbeat recoils with the method and apparatus presented in this disclosure.

Respiration modulates the heart rate due to respiratory sinus arrhythmia. The heart rate increases during inspiration and decreases during expiration. In other words, if the base value of the heart rate (prior to any influence by respiration) is steady at, for example, 80 beats per minute, then the heart rate may oscillate, with the respiration frequency, within an interval of 80±5 beats per minute due to respiratory sinus arrhythmia. This means that the adult heart rate may often be a fairly broad peak in the frequency domain.

The respiration rate determines both the frequency and the amplitude of respiratory sinus arrhythmia. It is therefore first necessary to determine the mother's respiration rate in a time interval where ballistocardiographic measurements are conducted. After that the base value and modulation of the mother's heart rate (for example, 80±5 beats per minute) can be determined from the ballistocardiographic data. These calculations are described in more detail in the examples below.

The terms "time domain" and "frequency domain" are known from the context of mathematical transformations which transfer a function (which may be measurement data stored as an array of discrete, time-stamped measurement results) from one of these domains to the other. Examples of such time/frequency domain transformations include Fourier series, Fourier transforms, Laplace transforms and Z transforms. In simplified terms, the term "time domain" can be understood as an arrangement of measurement data where the value of the measured variable is arranged as a function of measurement time. The term "frequency domain", on the other hand, can be understood as an arrangement of measurement data where the relative amplitudes of periodically recurring components in the measurement data are arranged as a function of their frequency.

The method presented in this disclosure may, for example, be implemented on discrete measurement data with a short-time Fourier transformation which is repeatedly conducted across a sliding time window. The time window can be updated for each new transformation. The transformation may be a Fast Fourier Transformation. Other suitable time/frequency domain transformations could also be used to implement the method presented in this disclosure.

An important requirement for the calculation is that it should produce heart rate estimates which facilitate continuous monitoring. This means that the determined heart rate indicator is preferably continuously updated based on the most recently measured data, so that abrupt changes can be noticed quickly. The time/frequency domain transformation for this reason advantageously a short-term transformation which covers only recently measured data. In other words, the transformation may be conducted repeatedly across a continuously updated and relatively narrow sliding time window, where the oldest measurement data points are removed as new data is added.

Continuous monitoring requires immediate calculations, but the transformations and calculations described in this disclosure may also be performed on older data sets, either for double-checking purposes or for experimenting with different variables pertaining to the transformation and calculation. The width of the time window in the short-time Fourier transformation may, for example, be fine-tuned by repeatedly changing its value and observing how the changes affect the calculations in a given data set. Other variables which may be optimized through experimentation on a fixed data set include, for example, the reliability weighting factor h, which is discussed in example 1 below.

An essential part of heart rate monitoring lies in comparisons between most recent data and data which was acquired earlier. All determined heart rate indicators may be stored in a time series which shows how the heart rate has developed since the start of the measurement. Earlier heart rate indicators need not be deleted as new ones are added.

However, although the analysis methods described in this disclosure are not limited only to real-time applications, and although the data produced by the analysis may retain its interest for a long period of time, the primary focus of this disclosure is to describe how heartbeats can be continuously monitored to detect abnormalities which might require a rapid response.

In this disclosure the term "time interval" refers to a time period where one indicator value can be determined for the test subject's heart rate. The test subject's heart rate in each time interval is calculated from the measurement data obtained within the bounds of this time interval. The resulting heart rate indicator may be stored with a time stamp. The time stamp may, for example, correspond to the beginning of the time interval. After this indicator has been stored, the time interval may be updated by sliding the time window one time step (for example, one second) forward. The measurement data which now falls outside of the time interval because it is too old is excluded, and new data obtained from the sensor is included at the other end of the time interval. A new heart rate indicator in this new time interval may then be calculated in the same way as the previous one. This calculation and updating procedure may be repeated continuously to produce a time series of heart rate indicators which can be monitored.

As already indicated, adjacent time intervals may overlap when the transformations are performed across a sliding time window. If, for instance, a first indicator of the test subject's heart rate is determined in a time interval from 2 seconds to 32 seconds, a second indicator may be determined in a time interval from 3 seconds to 33 seconds, a third indicator in a time interval from 4 seconds to 34 seconds, and so on. The time step between adjacent time intervals can be selected freely and optimized with basic experimentation.

At least two considerations may affect the choice of a suitable width for the time interval. A longer time interval allows more data to be collected and thereby produces a more reliable indicator. However, the objective of the method is to facilitate a rapid response in emergency situations. A long time interval will delay the onset of an alarm because a sudden drop in heart rate will be seen later if the indicator is calculated from a long-term data set. For example, if the width of the time interval would be 5 minutes, the data gathered during the past 15 seconds would constitute only 5% of the entire data set. If the heart rate suddenly drops, it may take several minutes until the new, low heart rate data changes the indicator sufficiently to trigger an alarm.

The method and apparatus of present disclosure may, for example, be implemented with a time interval which is 30 seconds wide. At least 20-30 heartbeat recoil peaks from each person will typically be present in data sets with this time interval. Practical experience has shown that this amount of data is sufficient for calculating reliable heart rate indicators. Furthermore, this time interval width facilitates an alarm to be triggered at least 20-25 seconds after a sudden drop in heart rate.

It may be noted that increasing the sampling frequency of the acceleration sensor will increase the resolution of the measurement only up to a certain point. The number of heartbeat recoils in the time interval stays the same no matter how frequently the acceleration sensor output is read. In other words, increasing the amount of measurement data by sampling the sensor more often may not always improve the reliability of the indicator.

In this disclosure, "screening the output signal in the frequency domain with the characteristics of dominant periodic components" means that the frequency domain data which corresponds to the frequencies of the dominant periodic components, including their modulation and their higher harmonics, is excluded from the subsequent heart rate calculation procedure. The screening and calculation procedures will be described in more detail below.

Figure 2:
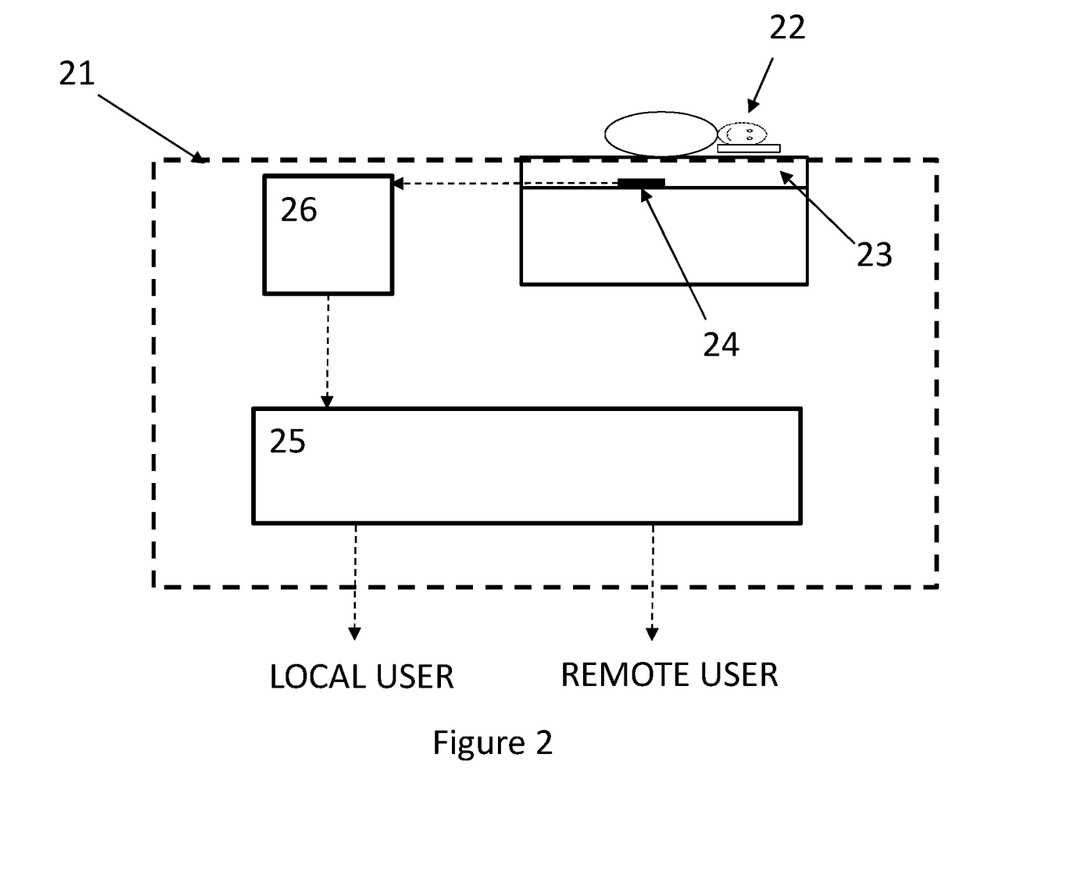
FIG. 2 illustrates a monitoring system described in this disclosure.

This disclosure also relates to a monitoring system 21 for monitoring the heartbeat of a test subject 22, illustrated in FIG. 2. The monitoring system comprises an acceleration sensor 24 configured to be held in contact with a recoil surface 23 which is in contact with the test subject 22. The monitoring system further comprises a control unit 26 which is connected to the acceleration sensor 24 to receive a sensor output signal in a time interval, and configured to calculate an indicator of the average heart rate of the test subject in the time interval. The monitoring system also comprises an interface unit 25 connected to the control unit 26 and configured to output the indicator for monitoring. The control unit 26 is configured to calculate the indicator by identifying in the time domain characteristic frequencies of dominant periodic components in the sensor output signal during the time interval, transforming the sensor output signal to the frequency domain across the time interval, screening the characteristic frequencies of dominant periodic components in the frequency domain, and calculating the indicator from the data which remains in the frequency domain after screening.

When the test subject is a fetus, the recoil surface 23 may be the mother's belly and the sensor 24 may be placed on the outside of the belly. This embodiment is not separately illustrated, but it can be implemented with a monitoring system which is similar to the one presented in FIG. 2. Only the placement of the sensor is different.

The acceleration sensor 24 can be any acceleration sensor with a sufficiently high resolution and sufficient frequency response to produce a signal in a ballistocardiographic measurement. The sensor may, for example, be a MEMS accelerometer.

The acceleration sensor 24, the control unit 26 and the interface unit 25 are communicatively coupled to each other. A communication link coupling the elements may include, for example, a Bluetooth, Wifi or wireless data link, or a wired data link.

The control unit 26 and the interface unit 25 may be separate elements, or parts of a computer device. The acceleration sensor 24 may be a separate element, or integrated to the computer device with the control unit 26 and/or the interface unit 25. The computer device may be a mobile phone, tablet computer, personal computer or the like, adapted to perform the methods of this disclosure. The control unit may comprise one or more data processors. The control unit 26 may be connected to a memory unit where computer-readable data or programs can be stored. The memory unit may comprise one or more units of volatile or non-volatile memory, for example EEPROM, ROM, PROM, RAM, DRAM, SRAM, firmware, programmable logic, or the like.

The monitoring system 21 performs a monitoring function by calculating the indicator in multiple, preferably successive, time intervals. The monitoring system may include a local automated monitoring node, as shown in FIG. 2. Alternatively, the monitoring system may include a local node and one or more remote nodes communicatively coupled to the local node. The local node may thus include the acceleration sensor 24, communicatively coupled to a control unit 26 and an interface unit 25 in a remote node to transfer sensor output signals for remote monitoring. Alternatively, the local node may include the acceleration sensor 24, the control unit 26, and the interface unit 25, communicatively coupled to a remote node, to output calculated indicators for remote monitoring in the remote node.

The methods described in the present disclosure may be implemented in, for example, hardware, software, firmware, special purpose circuits or logic, a computing device or some combination thereof. Software routines, which may also be called program products, are articles of manufacture and can be stored in any apparatus-readable data storage medium, and they include program instructions to perform particular predefined tasks. Accordingly, embodiments of this invention also provide a computer program product, readable by a computer and encoding instructions for performing the methods described in this disclosure.

A local node or a remote node may be configured to check the calculated indicator values, and/or the corresponding time derivatives, against predetermined threshold values. The interface unit 25 of a local node or a remote node may comprise loudspeakers or other sound units for outputting audible alarm signals to a local user if indicator values fall below or exceed a threshold value. The interface unit 25 may also comprise screens or displays for outputting calculated indicator values, such as the most recent indicator values or a history of indicator values, by presenting them to a local or remote user, and for given visible alarm signals if an indicator value falls below or exceeds a threshold value.

The method steps relating to identifying the characteristics of dominant periodic components and determining the heart rate of the test subject in the frequency domain after screening the output signal will now be described in more detail through the following examples.

EXAMPLE 1

In a first embodiment the test subject is a fetus inside a pregnant mother's belly. The recoil surface is the outside surface of the belly, where the acceleration sensor can be attached. The mother is usually lying down when the measurement is performed so that a clear ballistocardiographic signal can be recorded.

Time intervals where the mother moved will contain a lot of noise which conceals the heartbeat recoils. The measurement data gathered in these time intervals will normally have to be discarded. The control unit may, for example, detect these bodily movements by calculating signal-to-noise ratios in either the time domain or the frequency domain, and abort the calculation of a heart rate indicator in this time interval if the signal-to-noise ratio is below a certain threshold value. Other methods for discarding invalid measurement data may also be used. Both examples in this disclosure describe the analysis of high quality measurement data, measured when the test subject, the mother and/or the person lying next to the test subject did not perform any volitional movements which disturbed the measurement.

The dominant periodic component in the ballistocardiographic signal is the mother's heart rate, modulated by respiration as described above. The mother's respiration rate and heart rate should first be identified in the time domain.

The analysis may be performed on data measured in a time interval which may be 20-60 seconds long, preferably 30-40 seconds long. The analysis may be conducted repeatedly in a sliding time window. The time window can, for example, be updated by time steps of 1 second, and a new analysis may be calculated after each update.

All calculations in both the first and second embodiments may be performed on data measured from both axes of the acceleration sensor. When the acceleration sensor employed in the ballistocardiographic measurement is a two-axis sensor, the measurement data will comprise two time series, one set of data from the first axis (which may be labelled the x-axis) and another set of data from the second axis (which may be labelled the y-axis). The x-axis may be orthogonal to the y-axis. Both the x- and y-axis data can be analysed and the reliability of a heart rate indicator determined from each axis can, for example, be assessed from signal-to-noise ratios on each axis.

When an acceleration sensor is attached to a mother's belly, the ballistocardiographic measurement will be disturbed and concealed when the mother moves. Most of these disturbances may be classified as measurement noise, and ballistocardiographic heartbeat monitoring is usually restricted only to moments when the mother is still.

When the mother is lying still, the dominant movement influencing the acceleration sensor is the periodic breathing movement of the lungs, which also moves the surface of the belly. The mother's respiration rate may be detected as a change in the inclination of the acceleration sensor. The magnitude of the gravitational force along the x- and y-axes changes with each breath. This change in sensor inclination may be a very dominant periodic component in the measurement signal.

To facilitate a calculation of respiration frequency and depth, the control unit may first filter the DC-coupled sensor signal with both high- and low-pass filters. Many alternative filtering options are available, so the filtering described below is only exemplary. The control unit may apply the filters:

$$\text{high pass: } b(t) = (1-k_{HP}) \cdot [a(t) - a(t-1) + b(t-1)] \quad (1)$$

$$\text{low pass: } b(t) = b(t-1) - (1-k_{LP}) + k_{LP} \cdot a(t), \quad (2)$$

where t and t−1 are adjacent time steps in a time series, a(t) is the input (either the signal measured from the acceleration sensor or an already filtered version of that signal) at time t and b(t) is the filtered output at time t. The coefficients $k_{HP}$ and $k_{LP}$ are high and low pass filter coefficients, respectively.

With a suitably chosen high pass filter coefficient $k_{HP}$, the filtered output data b(t) obtains both negative and positive values. This facilitates a more versatile analysis, because the control unit can then calculate respiration frequencies either from peak to peak times or from the time gap between consecutive crossings of the horizontal (time) axis in either direction. Low pass filtering, on the other hand, removes noise from the output data. A Savitzky-Golay filter can also be applied to the data to remove spikes which cannot have their origin in heartbeat recoils.

Figure 3:
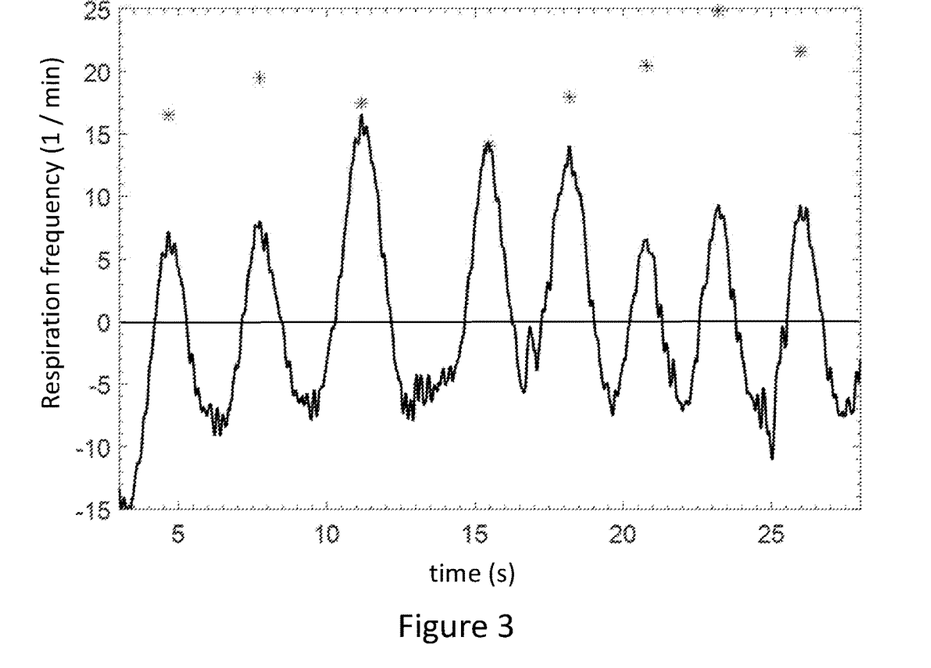
FIG. 3 shows ballistocardiographic data relating to a first embodiment in the time domain.

FIG. 3 shows exemplary DC-coupled and filtered measurement data from one measurement axis in a measurement conducted on the belly of a pregnant woman. The horizontal axis shows the measurement time in seconds. The solid line shows the measured DC-coupled acceleration sensor data after high- and low-pass filtering. This data has been scaled to the vertical axis in arbitrary units. The large periodic features of the signal are due to the mother's respiration, while the small variation includes heartbeat recoils.

The control unit can calculate the momentary respiration frequency from several periodically recurring time gaps in FIG. 3, either peaks or crossing-points. In FIG. 3 there is an asterisk above each peak. This asterisk shows, on the vertical axis, the respiration frequency corresponding to the time gap between this peak and the preceding one. The vertical axis shows the numerical values of these momentary respiration frequencies with the unit 1/min. The breathing frequency may be calculated from either x-axis or y-axis data, or from a combination of both data sets, such as the x+y sum. Respiration depths, which also influence heart rate modulation, are directly proportional to the peak heights.

Once the control unit has determined the momentary respiration frequencies, it may calculate an approximate respiration correction to the measured data. This may for example be done by expressing the respiration cycle in the sensor data as a function of time c(t). The function c(t) may be a series of smoothed functions, each fitted to the data between two peaks in FIG. 3. If the filtered ballistocardiographic measurement data is denoted with b(t) as above, a respiration-corrected set d(t) of ballistocardiographic data may then be calculated with the formula $$d(t)=b(t)-k_{RR} \cdot c(t) \tag{3}$$

where $k_{RR}$ is a numerical coefficient which depends on the filtering and signal amplification. A suitable coefficient $k_{RR}$ can be determined with basic experimentation.

The control unit may also store momentary respiration frequencies to calculate the respiration modulation of the mother's heart rate.

Figure 4:
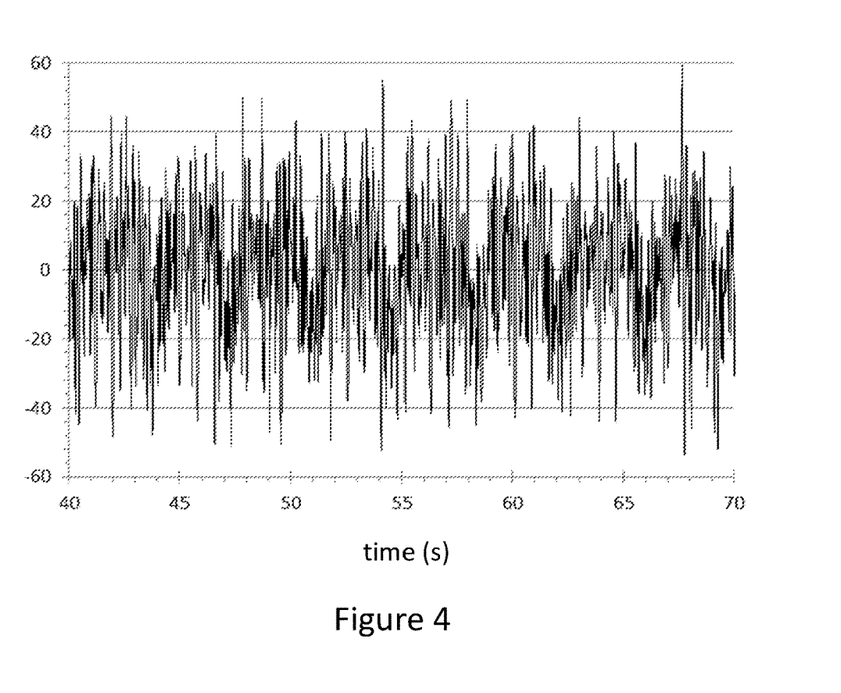
FIG. 4 shows ballistocardiographic data relating to a first embodiment in the time domain.

FIG. 4 shows AC-coupled measurement data d(t) after the control unit has calculated an approximate respiration correction. The unit on the vertical axis is arbitrary. The illustrated AC-coupled data was filtered with high- and low-pass filters before the respiration correction was applied. The high- and low-pass filtering of the AC-coupled measurement data may be performed with the formulas 1 and 2 presented above, but the filter coefficients $k_{HP}$ and $k_{LP}$ used for AC-coupled data may differ from the coefficients which were used to filter DC-coupled data.

In FIG. 4 the dominant peaks in the measurement data are due to adult heartbeat recoils. It is evident from the data that the approximate respiration correction was not perfect. A periodic variation corresponding to the respiration frequency is still visible in the data. However, the control unit may identify in the time domain the characteristic frequencies of dominant periodic components even if a little respiration-induced variation still remains. When the dominant periodic component is a heart rate, as in the present case, it may be detected in the illustrated time interval from 40 seconds to 70 seconds in FIG. 4 for example by detecting periodic components with an approximately constant amplitude (±20% may for example be applied as a limit for amplitude variation) and an approximately constant frequency (±150 ms between beat-to-beat times may be applied as a limit).

The mother's heart rate (HR) and respiration rate (RR) identified by the control unit represent approximate averages during the time interval. The modulation of the heart rate takes the form $HR \pm k_{MOD} \cdot RR$, where $k_{MOD}$ is a coefficient which can be calculated from the respiration amplitude identified from the data in FIG. 3.

Once the control unit has identified the characteristic frequencies of dominant periodic components, that is, once it has estimated the heart rate and respiration rate of the mother in the time interval, the measurement data may be transformed to the frequency domain with a discrete short-time Fourier transformation across the time interval. This can, for example, be performed by executing a Matlab Fast Fourier Transformation on the measurement data which ranges from the beginning of the time interval to the end of the time interval.

In the frequency domain, the mother's heart rate and respiration rate plus their periodic modulation and their harmonics (especially the second harmonic, but possibly higher ones as well) constitute frequency ranges where the infant's heart rate may be obscured. The control unit screens the output signal in the frequency domain by excluding these frequency ranges when the fetus heart-rate indicator is calculated in this time interval. The rest of the data in the frequency domain is used in the calculation.

Figure 5:
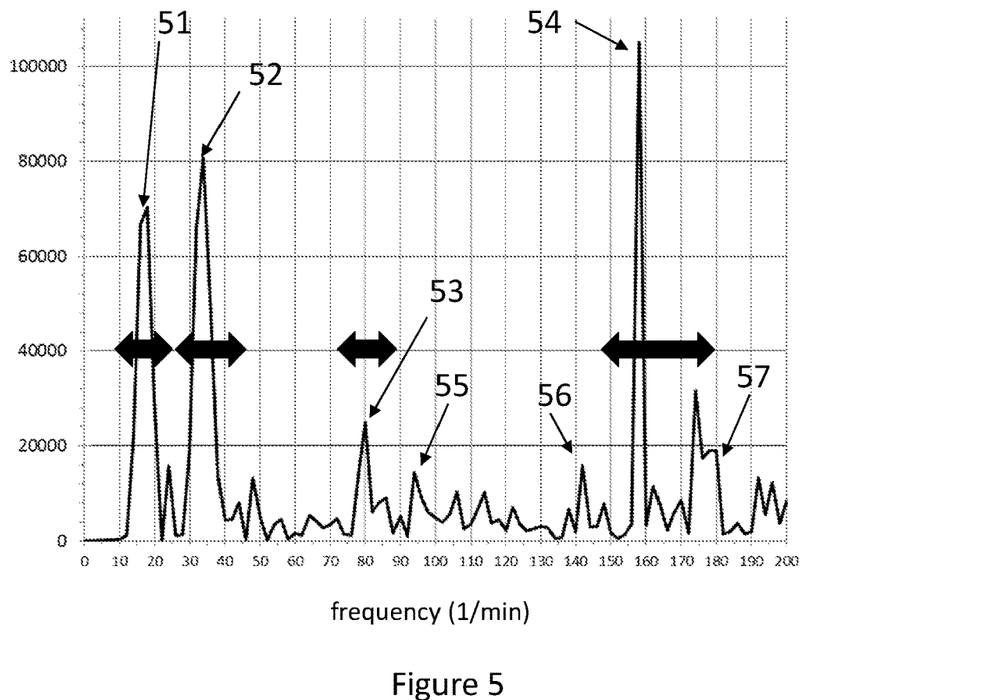
FIG. 5 shows ballistocardiographic data relating to a first embodiment in the frequency domain.

FIG. 5 shows, in the frequency domain, the same data which was presented in the time domain in FIG. 4. The unit on the vertical axis is again arbitrary. The mother's respiration rate, at approximately 16-17/min, corresponds to peak 51 and its second harmonic corresponds to peak 52.

The excluded data is approximately indicated by the black arrows in FIG. 5. The respiration frequency and its second harmonic may be excluded simply by removing all data below a frequency of 40 beats per minute. This exclusion does not require much precision because these frequencies are not close to the expected fetus heart rate.

Based on the analysis in the time domain, the peak 53 in FIG. 5 may be interpreted as the mother' heart rate in the frequency domain. The frequencies around this peak may be excluded by removing all the measurement data which falls within the modulation limits [HR—k·RR, HR+k·RR]. Alternatively, the excluded frequency range may extend beyond the modulation limits to the first local minimum after the modulation limit. The excluded frequency range around the second harmonic peak 54 is calculated simply by multiplying the excluded frequencies around peak 53 by two.

Figure 6:
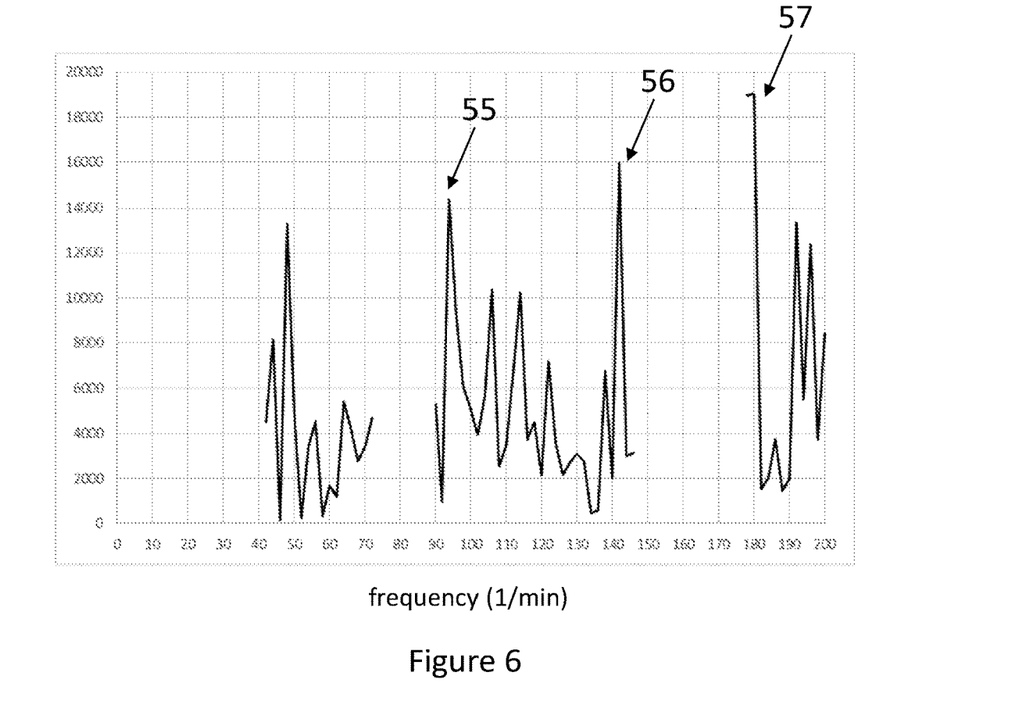
FIG. 6 shows ballistocardiographic data relating to a first embodiment in the frequency domain.

FIG. 6 illustrates the same measurement data which was shown in FIG. 5, where the characteristic frequencies of the dominant periodic components have been screened so that no measurement data is shown for these frequencies. The unit on the vertical axis is again arbitrary, but it is the same arbitrary unit as in FIG. 5.

As seen in FIG. 6, there are multiple peaks in the measurement data, including peaks 55 and 56 which are visible in FIG. 5. Multiple peaks may arise if the fetus' heart rate changes during the time interval, so several peaks may in fact represent correct heart rates. Alternatively, one peak may be the correct fetus heart rate (which has remained approximately constant in the time interval) and the other peak(s) may be measurement noise arising from an unknown source.

The control unit may start the calculation of a heart rate indicator F(t) for the time interval with the timestamp t by determining which peaks should be retained for the calculation and which should not. The number of retained peaks will be labelled m in the analysis below. The control unit may, for example, select these peaks and determine the value m based on criteria such as the height of the peaks, the relative heights of lower peaks in relation to the highest, the proximity of each peak to a heart rate indicator F(t−1) calculated earlier, or a combination of these criteria. The peaks which best fit the selection criteria may be retained for the calculation.

The data in FIG. 6 includes peak 57 which has been partly screened, so that no local minimum exists on its left side. Such peaks may be excluded from the indicator calculation with a requirement demanding that local minima must be present on both sides of the peaks which are included in the calculation. The requirement may also be that both sides of a peak must comprise measurement data which lies below 50% of the height of this peak.

If m>1, an average heart rate estimate $F_E(t)$ may, for example, be calculated as a weighted average $$F_E(t) = \frac{x_1^n f_1 + \ldots + x_m^n f_m}{x_1^n + \ldots + x_m^n} \quad (4)$$

where $f_1$ is the frequency corresponding to the first peak and $x_1$ is its height, and $f_m$ is the frequency corresponding to the m:th peak and $x_m$ is its height. All of these values are obtained from the frequency domain data which corresponds to the timestamp t. The number n in formula 4, which may obtain integer values from zero upwards, is a parameter which the person skilled in the art can optimize through experimentation. It determines how much differences in peak heights should be emphasized.

In other words, the average heart rate estimate may be calculated as a weighted average which is based on the characteristics of the various peaks in the frequency domain after screening. This automated calculation produces sufficiently reliable results even in the presence of some uncertainties in the measurement data, such as multiple correct test subject heart rate peaks in the frequency domain.

The control unit may then calculate the indicator F(t) as a recursive weighted average with the formula $$F(t)=F(t-1)\cdot(1-h)+h\cdot F_E(t) \quad (5)$$

where h is a reliability weighting factor which determines how much weight the new average heart rate estimate $F_E$ should be given in relation to the previously calculated indicator value F(t−1). The indicator F(t−1) may also be replaced with an indicator calculated in any previous time interval. When the very first indicator value is calculated (that is, when no previous calculation result is available), the factor h may obtain the value 1 by default.

Alternatively, the indicator may be calculated as a recursive weighted average with a more general formula where j earlier indicator values F(t−1), F(t−2), F(t−3) F(t−j) are included:

$$F(t) = \frac{\sum_{i=1}^{j} F(t-i)\cdot h_i}{j} + h\cdot F_E(t) \quad (6)$$

where $h_i$ is the reliability weighting factor of the i:th average heart rate estimate and h is the reliability weighting factor of the most recent average heart rate estimate, calculated at time t. The earlier indicator values need not necessarily be consecutive.

In other words, the control unit may calculate the indicator F(t) of the test subject's heart rate as a weighted average of one or more indicators F(t−1) calculated in previous time intervals and the average heart rate estimate calculated in the present time interval. In this context, the term "present" is used merely to distinguish the time interval with the timestamp t from preceding time intervals with timestamps t−1, t−2, t−3, and so on. In other words, the word "present" refers to the time interval with timestamp t, for which an indicator is calculated at present. The "present" in this sense may not correspond to the present moment because indicators may be calculated from data which has been recorded earlier. And even if the indicator is calculated immediately after all the data belonging to the time interval has been measured, there may still be a time gap between the timestamp t and the present moment if timestamps are assigned based on the beginning of each time interval.

The control unit may use various criteria for calculating the reliability weighting factors h. These criteria may, for example, include (1) the signal-to-noise ratio of the measurement data remaining in the frequency domain after the frequencies of the dominant periodic components have been screened, (2) the selected number m, (3) the peak heights $x_1$, $x_2$, $x_m$ in the measurement data which remains after screening, and/or (4) the total power density which remains in the measurement data after screening. The reliability weighting factor h may be calculated as a weighted average based on these criteria. The weighting of various criteria can also be performed through a Kalman filter.

In both examples the interface unit may be programmed to give an alarm if the fetus' heart rate indicator drops below a certain limit, or if it changes very rapidly in any direction.

Example 2

In a second embodiment the test subject is an infant sleeping on the same recoil surface as an adult. In this measurement situation the dominant periodic components in the ballistocardiographic signal usually stem from the adult's heartbeat and respiration. The characteristics which the control unit identifies in the time domain are therefore the heart rate and respiration rate of the adult.

As in the first example, the control unit identifies the heart rate and respiration rate of the adult separately in each time interval. The heart rate and respiration rate represent approximate averages during the time interval.

The acceleration sensor which is placed in contact with the recoil surface may be a two-axis sensor, with measurement axes x and y. The bodies of the infant and adult may both be aligned with the x-axis or the y-axis, or one of them may be aligned with the x-axis and the other with the y-axis. All sorts of intermediate positions, which deviate from x- and y-axes by angles between 0° and 90°, are of course also possible. A person's heartbeat recoil may be visible in both the x- and y-axis measurement data, but possibly stronger on the axis from which the body position deviates less. The signal-to-noise ratio may consequently be higher in the data gathered from one measurement axis than in the data gathered from the other. Based on signal-to-noise ratios, for example, the control unit may select one measurement axis for calculating the infant's heart rate indicator, or combine data from both axes.

In this measurement, respiration does not turn the sensor as in the first example because the sensor is not attached to a human body. Respiratory movements are therefore not as dominant in the measurement signal as in FIG. 3.

The control unit may calculate the respiration rate of the adult either from momentary heart rates or heart stroke volumes. Since respiration modulates the heart rate, the respiration rate can be calculated from periodic variations in the momentary heart rate. Respiration also modulates the heart stroke volume, so that stroke volume decreases during inspiration and increases during expiration. The volume of a heart stroke is proportional to the amplitude of the corresponding peak in the ballistocardiographic data. If the base value for the stroke volume remains constant, the respiration frequency determines a periodic variation in stroke volume. The respiratory modulation in heart stroke volume can be detected as a periodic amplitude variation in the ballistocardiographic signal. The corresponding respiration rate and respiration depths can be calculated through extrapolation.

Adult heartbeat recoils may be identified in the ballistocardiographic data with the method described in the first example, in other words by detecting periodic components with an approximately constant amplitude (±20% may for example be applied as a limit for amplitude variation) and an approximately constant frequency (±150 ms between beat-to-beat times may be applied as a limit).

The respiration rate may then be calculated from beat-to-beat times (the time intervals between consecutive heartbeats). By plotting all beat-to-beat times as a function of time, the periodicity arising from the respiration can de observed and the respiration rate can be calculated. The respiration rate can also be calculated from the period variation of heartbeat peak amplitudes. Respiration rates calculated with these two methods may be compared and/or averaged.

Once the control unit has identified the adult heart rate and respiration rate in the time interval, the measurement data may be transformed to the frequency domain with a discrete short-time Fourier transformation across the time interval, as described in the first example above.

In the frequency domain, the adult heart rate and respiration rate plus their periodic modulation and their harmonics are screened in the manner described in the first example. The control unit screens the output signal in the frequency domain by excluding these frequency ranges and retaining the rest of the data for analysis. Once the dominant periodic components have been screened in the frequency domain, the control unit may calculate the indicator of the infant's heart rate in the manner described in the first example.

In both embodiments, the control unit performs the screening process separately in each time interval. In other words, frequencies which were excluded from the determination procedure in one time interval are not thereby excluded from the determination in any subsequent (or preceding) time interval.

All calculations mentioned in these examples can be performed on both the x-axis and y-axis data. The control unit may compare or add data from both axes when the indicator of the infant heart rate is calculated.

FURTHER EXAMPLES

Ballistocardiographic measurements can also be obtained from a recoil surface when the infant lies on it alone. The infant's heart rate can in this case be determined directly from peak-to-peak intervals. Measurements conducted when no adult is present can be helpful for identifying the infant heart rate peak in a subsequent measurement situation where an adult is present in the same bed. The measurement with no adult present may, for example, indicate what signal strength one can expect in the infant heartbeat recoils. This may have implications for the weights assigned to various criteria when the control unit calculates the indicator of the infant heart rate.

The methods described in the embodiments above are also applicable when dominant periodic components in the measurement data (with frequencies close to the test subject's heart rate) arise from other sources, such as a mechanical apparatus which is in contact with the recoil surface.

The methods described in the embodiments above can also be applied to two persons of approximately equal size, lying on the same recoil surface. The two persons may be two adults, two infants or two children. The heartbeat recoils of both persons will then be of approximately equal size. If the acceleration sensor is placed closer to the area where the first person is lying, and thereby further from the area where the second person is lying, then the heartbeat recoil of the first person will be the dominant periodic component and the second person becomes the test subject whose heart rate can be determined in the frequency domain after the frequency data has been screened with the characteristics of the dominant periodic component. It is, of course, also possible to use two separate acceleration sensors in these situations, one closer to the first person and another sensor closer to the second person. Using two sensors in an adult/infant measurement setting is not equally helpful because the adult's heartbeat recoil may dominate the measurement signal in both sensors and infants tend to move around a lot as they sleep.

The invention claimed is:

1. A method for monitoring a heart rate of a test subject, comprising:
    placing an acceleration sensor or an angular rate sensor in contact with a recoil surface which is in contact with the test subject to measure movements due to heartbeat recoils in the test subject,
    measuring a sensor output signal in multiple time intervals,
    calculating from the sensor output signal measured in a time interval an indicator of an average heart rate of the test subject in said time interval, and
    outputting the indicator for monitoring,
    wherein the calculation includes:
    identifying in a time domain characteristic frequencies of dominant periodic components in the sensor output signal during the time interval,
    transforming the output signal to a frequency domain across the time interval,
    screening the characteristic frequencies of dominant periodic components in the frequency domain, and
    calculating the indicator from the data which remains in the frequency domain after screening, wherein the recoil surface is flat, the test subject is lying on the recoil surface when the measurement is performed, and the test subject is an infant sleeping on the recoil surface with an adult and the dominant periodic components include a second harmonic of the adult's heart rate.

2. A method according to claim 1, wherein the acceleration sensor or the angular rate sensor is a 2-axis acceleration sensor.

3. A method according to claim 1, wherein the indicator is calculated as a weighted average of
    one or more indicators calculated in earlier time intervals, and an average heart rate estimate calculated in a present time interval.

4. A monitoring system for monitoring a heartbeat of a test subject, the monitoring system comprising:
an acceleration sensor or an angular rate sensor configured to be held in contact with a recoil surface which is in contact with the test subject to measure movements due to heartbeat recoils in the test subject,
a control unit connected to the acceleration sensor or the angular rate sensor to receive a sensor output signal in a time interval, and configured to calculate an indicator of an average heart rate of the test subject in the time interval,
an interface unit connected to the control unit and configured to output the indicator for monitoring,
wherein the control unit is configured to calculate the indicator by:
identifying in a time domain characteristic frequencies of dominant periodic components in the sensor output signal during the time interval,
transforming the sensor output signal to a frequency domain across the time interval,
screening the characteristic frequencies of dominant periodic components in the frequency domain, and
calculating the indicator from the data which remains in the frequency domain after screening, wherein the recoil surface is a flat surface on which a test subject can lie, the test subject is lying on the recoil surface when the measurement is performed, and the test subject is an infant sleeping on the recoil surface with an adult and the dominant periodic components include a second harmonic of the adult's heart rate.

5. A monitoring system according to claim 4, wherein the acceleration sensor or the angular rate sensor is a 2-axis acceleration sensor.

6. A monitoring system according to claim 4, wherein the control unit is configured to calculate indicator as a weighted average of
one or more indicators calculated in earlier time intervals, and
an average heart rate estimate calculated in the present time interval.

7. A method for monitoring a heart rate of a test subject, comprising:
placing an acceleration sensor or an angular rate sensor in contact with a recoil surface which is in contact with the test subject to measure movements due to heartbeat recoils in the test subject,
measuring a sensor output signal in multiple time intervals,
calculating from the sensor output signal measured in a time interval an indicator of an average heart rate of the test subject in said time interval, and
outputting the indicator for monitoring,
wherein the calculation includes:
identifying in a time domain characteristic frequencies of dominant periodic components in the sensor output signal during the time interval,
transforming the output signal to a frequency domain across the time interval,
screening the characteristic frequencies of dominant periodic components in the frequency domain, and
calculating the indicator from the data which remains in the frequency domain after screening, wherein the recoil surface is the outside of a mother's belly, the test subject is inside the belly when the measurement is performed, and the dominant periodic components include a second harmonic of the mother's heart rate.

8. A monitoring system for monitoring a heartbeat of a test subject, the monitoring system comprising:
an acceleration sensor or an angular rate sensor configured to be held in contact with a recoil surface which is in contact with the test subject to measure movements due to heartbeat recoils in the test subject,
a control unit connected to the acceleration sensor or the angular rate sensor to receive a sensor output signal in a time interval, and configured to calculate an indicator of an average heart rate of the test subject in the time interval,
an interface unit connected to the control unit and configured to output the indicator for monitoring,
wherein the control unit is configured to calculate the indicator by:
identifying in a time domain characteristic frequencies of dominant periodic components in the sensor output signal during the time interval,
transforming the sensor output signal to a frequency domain across the time interval,
screening the characteristic frequencies of dominant periodic components in the frequency domain, and
calculating the indicator from the data which remains in the frequency domain after screening, wherein the surface is the outside of a belly of a mother with the test subject inside the belly when the measurement is performed, and the dominant periodic components include a second harmonic of the mother's heart rate.

* * * * *